(12) United States Patent
Desser et al.

(10) Patent No.: US 8,231,870 B2
(45) Date of Patent: Jul. 31, 2012

(54) PHARMACEUTICAL PREPARATION FOR TREATING BENIGN PROSTATIC HYPERPLASIA

(75) Inventors: Lucia Desser, Vienna (AT); Bernhard Lotz, Leonding (AT); Thomas Mohr, Guntramsdorf (AT)

(73) Assignee: Volopharm GmbH, Wels (AT)

( * ) Notice: Subject to any disclaimer, the term of this patent is extended or adjusted under 35 U.S.C. 154(b) by 177 days.

(21) Appl. No.: 12/745,776

(22) PCT Filed: Dec. 3, 2008

(86) PCT No.: PCT/AT2008/000428
§ 371 (c)(1),
(2), (4) Date: Jun. 2, 2010

(87) PCT Pub. No.: WO2009/070818
PCT Pub. Date: Jun. 11, 2009

(65) Prior Publication Data
US 2010/0254968 A1   Oct. 7, 2010

(30) Foreign Application Priority Data
Dec. 3, 2007   (AT) ................ A 1962/2007

(51) Int. Cl.
*A61K 38/48* (2006.01)
(52) U.S. Cl. .................................. 424/94.64
(58) Field of Classification Search ............ 424/94.64
See application file for complete search history.

(56) References Cited

U.S. PATENT DOCUMENTS

| | | |
|---|---|---|
| 2003/0194400 A1 | 10/2003 | Liu et al. |
| 2006/0024385 A1 | 2/2006 | Pedersen et al. |

FOREIGN PATENT DOCUMENTS

| | | |
|---|---|---|
| WO | WO-90/08555 A1 | 8/1990 |
| WO | WO-94/19005 A1 | 9/1994 |
| WO | WO-2006/127431 A2 | 11/2006 |
| ZA | 200002342 A | 1/2001 |

OTHER PUBLICATIONS

Azzouzi et al., Other therapies for BPH patients: desmopressin, anticholinergic, anti-inflammatory drugs, and botulinum toxin. World J Urol. Sep. 2006;24(4):383-8. Epub May 18, 2006.
Lissbrant et al., Neutralizing VEGF bioactivity with a soluble chimeric VEGF-receptor protein flt(1-3)IgG inhibits testosterone-stimulated prostate growth in castrated mice. Prostate. Jan. 1, 2004;58(1):57-65.
Madersbacher et al., [Benign prostate hyperplasia: success and limitations of pharmacological therapy] Internist (Berl). Oct. 2007;48(10):1157-64. German. English translation provided.
Maurer, Bromelain: biochemistry, pharmacology and medical use. Cell Mol Life Sci. Aug. 2001;58(9):1234-45.
Ransberger, Enzymtherapie des Krebses. [Enzyme therapy of cancer]. Sonderdruck aus Erfahrungsheilkunde. 1971;1:14-17. German. English translation provided.
Stefanou et al., Expression of vascular endothelial growth factor (VEGF) and association with microvessel density in benign prostatic hyperplasia and prostate cancer. In Vivo. Mar.-Apr. 2004;18(2):155-60.
Trapeznikova et al., [Vascular endothelial growth factor in patients with prostate cancer and benign prostatic hyperplasia]. Vestn Ross Akad Med Nauk. 2005;(5):14-16. Russian. English translation provided.
Verhamme et al., Triumph Pan European Expert Panel. Incidence and prevalence of lower urinary tract symptoms suggestive of benign prostatic hyperplasia in primary care-the Triumph project. Eur Urol. Oct. 2002;42(4):323-8.
Walsh et al., Distribution of vascular endothelial growth factor (VEGF) in prostate disease. Prostate Cancer Prostatic Dis. 2002;5(2):119-22.
Wilt et al., Phytotherapy for benign prostatic hyperplasia. Public Health Nutr. Dec. 2000;3(4A):459-72.

*Primary Examiner* — Maryam Monshipouri
(74) *Attorney, Agent, or Firm* — Wolf, Greenfield & Sacks, P.C.

(57) ABSTRACT

The present invention relates to the use of at least one protease for the manufacture of a medicament for the treatment and/or prevention of benign prostate hypertrophy/hyperplasia, wherein the medicament is adapted for enteral administration, the at least one protease is selected from the group consisting of plant, non-mammalian animal and microbial proteases and the at least one protease is administered in an amount of 1 to 100 mg/kg body weight.

11 Claims, 4 Drawing Sheets

PHARMACEUTICAL PREPARATION FOR TREATING BENIGN PROSTATIC HYPERPLASIA

RELATED APPLICATIONS

This application is a national stage filing under 35 U.S.C. §371 of international application PCT/AT2008/000428, filed Dec. 3, 2008, designating the United States of America, and which was published under PCT Article 21(2) in English.

The present invention relates to a medicament for the treatment of benign prostatic hyperplasia. Angiogenesis is the process by which the preexisting vasculature is modified to establish a complex network of new blood vessels to support growing tissue. First, local release of ECM proteases by EC degrade the blood vessel's basement membrane. Second, activated EC invade the stroma, proliferate and form tubular structures that join together. Finally the basement membrane is resynthesized and pericytes migrate to the site of newly formed capillaries. Angiogenesis plays a role in a variety of physiological processes (embryogenesis, wound healing) and contributes to the progress of several pathological conditions (cancer, hyperplasia). Normally, endothelial cells in adult mammals are resting and divide only every few years. Under pathological conditions like benign prostatic hyperplasia, mastopathy, rheumatoid arthritis, arteriosclerosis, endometriosis, psoriasis, cancer or ocular neovascularization growth of endothelial cells is locally greatly enhanced.

Angiogenesis is regulated by a large number of pro- and antiangiogenic factors including placental growth factor (PlGF), fibroblast growth factors, Angiopoietins and others. The major limiting step in this process, however, seems to be the vascular endothelial growth factor (VEGF). Originally described as factor causing substantial vascular leakage and named Vascular Permeability Factor (VPF), this growth factor was later renamed Vascular Endothelial Growth Factor (VEGF) on account of its mitogenic effect in endothelial cells.

In a variety of in vitro and in vivo models, VEGF has been found to promote vascular endothelial cell growth and formation of blood vessels. VEGF also serves as a survival factor for endothelial cells. In vitro, VEGF prevents apoptosis induced by serum withdrawal. In vivo, VEGF inhibition in neonatal, but not in adult mice leads to extensive apoptotic changes in the vasculature. Knocking out VEGF-A in mice (either null [VEGF-A-/-]) or heterozygotic [VEGF-A+/-] forms) results in embryonic lethality between d 11 and d 12 with developmental abnormalities, defective vascularization in several organs and a markedly reduced number of nucleated red blood cells in the blood islets of the yolk sac, suggesting that VEGF-A controls both vasculogenesis and early hematopoiesis. Finally, VEGF induces vascular leakage and endothelial fenestration in adrenal endothelial cells.

Expression of VEGF can be induced by Hypoxia via the activation of the Hypoxia-inducible factor-1 (HIF-1). Lack of oxygen—caused for instance by excessive tissue growth—activates the expression of HIF-1. Subsequently, HIF-1 complexes accumulate in the cell nucleus, bind to the HIF-1 binding site of the DNA, and initiate respectively upregulate transcription of VEGF-mRNA triggering an angiogenic switch that may cause adjacent blood vessels to sprout into the hypoxic tissue. Various proinflammatory cytokines are also capable of inducing VEGF expression, thus explaining the role of angiogenesis in primarily inflammatory diseases such as psoriasis or rheumatoid arthritis.

With the recognition of this key role in the regulation of angiogenesis, VEGF and it's receptors have emerged as an interesting therapeutic target. Several strategies to interfere with VEGF mediated angiogenesis have been utilized mainly in cancer, but also in other diseases characterized by enhanced angiogenesis (e.g. Macular degenaration or benign prostatic hyperplasia). Drugs tested included antibodies, toxin conjugates, interfering peptides, soluble receptors and tyrosine kinase inhibitors. Taken together these results suggest that drugs targeted at VEGF will improve future therapies in diseases like cancer, rheumatoid arthritis, psoriasis and ocular neovascularisation and others.

Benign prostatic hyperplasia (BPH) refers to the increase in size of the prostate in middle-aged and elderly men. When sufficiently large, the enlarged prostate compresses the urethral canal and causes partial, sometimes even complete obstruction of the urethra, thus inhibiting the normal flow of urine. In severe cases the gland can reach up to ten times the normal size. BPH is not considered to be a premalignant lesion, but may become a considerable health problem for older men, mainly due to the negative effects on quality of life such as urinary hesitancy, frequent urination, increased risk of urinary tract infections and urinary retention.

BPH is relatively slowly progressing condition, requiring decades for the patient to develop symptoms related to the disease. However, by the age of 60 years, up to 50% of the male population has pathological BPH. Verhamme et al., Eur Urol. 2002 October; 42(4):323-8 described an incidence rate of BPH in 3/1000 man per year between the age of 45 and 49 years, reaching a maximum of 38 cases per 1000 man per year in the age group 75-79 years. In men older than 80 years, the incidence rate remained constant.

Currently there are three therapeutical options in treating BPH:

1. "Watchful waiting" is recommended if symptoms are mild and do not affect a man's quality of life. Individuals may also select this treatment option if they feel drug therapy may be a greater inconvenience than the symptoms of BPH. If symptoms occur and cause discomfort, affect activities of daily living, drug treatment is recommended.

2. Drugs are used to relieve the common urinary symptoms associated with BPH by either reducing the size of the prostate gland or slowing the growth of the prostate (Madersbacher et al. Internist (Berl.). 2007 Apr. 11). Common drug classes used to treat urinary symptoms include α blockers, such as doxazosin (Cardura) [side effects: Dizziness, drowsiness, light headedness, headache, constipation, loss of appetite, dry mouth, tiredness, stuffy nose, blurred vision, dry eyes or trouble sleeping], tamsulosin (Flomax) [side effects: a drop in blood pressure resulting in syncope or fainting; dizziness, headache, nasal congestion, and heart palpitations], 5-α reductase inhibitors, such as finasteride (Proscar) [side effects: Decreased amount of semen per ejaculation, decreased sex drive, impotence] or dutasteride (Avodart) [side effects: Breast tenderness, decreased sex drive, ejaculation problems, enlarged breasts in males, hives, impotence, itchy spots, rash].

3. In case of severe symptoms of BPH such as recurrent urinary retention, recurrent blood in the urine, recurrent urinary tract infections or bladder stones, the method of choice is the surgical removal of the prostate (prostatectomy). Side effects of prostatectomy include an additional risk of infections, perforation of the bladder, deep vein thrombosis, and total incontinence.

WO 90/08555 relates to the use of hydrolytic enzymes like proteases such as trypsin, chymotrypsin or bromelain for the treatment of prostata hypertrophy. The preparation according to said document is administered by a direct intraprostatic injection.

In the WO 2006/127431 a method of treating an individual suffering from prostata hypertrophy is disclosed. In the cause of said treatment mammalian enzymes like trypsin are administered.

ZA 200002342 relates to the use of plant sterines and its glucosides for the prevention of benign prostata hypertrophy. In order to increase the absorption rate of the plant sterines proteases like bromelain are added to said pharmaceutical compositions.

US 2006/0024385 relates to compositions which are applied to reduce oxidative stress. Said compositions may comprise plant extracts which may contain among other substances also bromelain.

US 2003/0194400 relates to compositions comprising selective tissue vascular thrombogen which can be bound to tissue associated with prostata hyperplasia.

In the WO 94/019005 pharmaceutical composition comprising one or more substances proteases are disclosed. In said document the proteases to be used include trypsin, chymotrypsin, bromelain, papain and ficin.

It is an object of the present invention to provide medicaments for treating or preventing benign prostate hyperplasia which overcome the drawbacks of the regularly used therapy forms and medicaments.

The present invention relates to the use of at least one protease for the manufacture of a medicament for the treatment and/or prevention of benign prostate hypertrophy/hyperplasia, wherein the medicament is adapted for enteral administration, the at least one protease is selected from the group consisting of plant, non-mammalian animal and microbial proteases and the at least one protease is administered in an amount of 1 to 100 mg/kg body weight.

It was surprisingly found that in particular a medicament comprising a combination of at least one protease, which is selected from the group consisting of plant, non-mammalian animal and microbial proteases, allows—when administered to an individual—to reduce significantly (at least 40%, preferably at least 50%, more preferably at least 60%, even more preferably at least 70%, most preferably at least 80%, in particular at least 90%, compared to the VEGF level of said individual prior the administration of the medicament according to the present invention) the level of VEGF and, thus, reducing angiogenesis. The reduction of angiogenesis is beneficial for preventing and treating benign prostate hyperplasia/hypertrophy in an individual.

This effect is even more surprising because the medicament comprising at least one protease is enterally (preferably orally or rectally) administered and the dose of 1 to 100 mg protease/kg body weight (equals 3-300 Units/kg body weight) is low. In the prior art, in particular in the WO 90/08555, it is suggested to inject proteases directly in the prostate in order to destroy the hyperplasic tissue. However the noninvasive enteral systemic administration of proteases to an individual in an amount according to the present invention surprisingly turned out to be sufficient to treat and prevent benign prostate hyperplasia/hypertrophy although of course being applied in a dose far below the dose for destroying human tissue (WO 90/08555). A combination of more than one protease, in particular of at least two (preferably at least three, at least four, at least five, at least six), proteases increases even more the therapeutic effect of preventing and/or treating benign prostate hyperplasia in an individual.

It turned surprisingly out that the combination of at least two proteases allows to treat more efficiently benign prostate hypertrophy/hyperplasia than the use of one single protease.

The prostate gland is androgen-dependent in that it requires testosterone for its normal growth, development, differentiation and function and androgen deprivation will decrease the size of the prostate. Anti-androgen therapies to reduce prostate overgrowth have only limited effects, therefore it is proposed that the steroids may permit rather than cause the prostatic growth. Evidence has emerged that prostatic growth may be under the immediate control of specific growth factors like VEGF and TGF-beta and may be only indirectly modulated by androgens.

BPH is characterized by hyperplasia of prostatic stromal and epithelial cells and an elevated microvessel density (Stefanou et al. In Vivo. 2004 March-April; 18(2):155-60). Androgens stimulate the start of hypertrophy of the cells in the prostate. Hypertrophy over time may result in regional hypoxia, which induces the expression of hypoxia factors (HIF-1 and HIF-2). HIF stimulates the synthesis of VEGF in the epithelial cells of the prostate (Walsh et al. Prostatic Dis. 2002; 5(2):119-22) The increased expression of VEGF may induce angiogenesis and consequently lead to clinical progression of BPH resulting in the formation of large, fairly discrete nodules in the periurethral region of the prostate. Interruption of this continuum could reduce hyperplasia.

Targeting VEGF therefore represents a potential direct therapeutic approach to the regulation of abnormal enlargement of the prostate and possible also to the amelioration of the symptoms associated with benign prostate hyperplasia. VEGF serum concentration is elevated in BPH in comparison to healthy controls but significant smaller compared to patients with prostate cancer (Trapeznikova et al. Vestn Ross Akad Med Nauk. 2005; (5):14-6).

Angiogenesis is elevated in BPH, is more pronounced in prostate cancer and correlates with VEGF concentration (Stefanou et at. In Vivo. 2004 March-April; 18(2):155-60). Anti-VEGF reduces angiogenesis in prostate of castrated, testosterone treated rats (Lissbrant et al. Prostate. 2004 Jan. 1; 58(1):57-65).

According to the present invention the terms "benign prostate hypertrophy" and "benign prostate hyperplasia" define the same disease and can hence be used within the scope of the present invention interchangeable.

The administration of proteases from bacteria, fungi, plants and non-mammalian animals is especially suited because said proteases do not show significant toxicity when contacted with human or animal cells, in particular with endothelial cells. Even a combination of proteases as disclosed herein is not toxic to an animal or human, but acts on angiogenesis.

Interestingly, it could be shown that proteases of mammalian (i.e. humans) origin are not able to efficiently inhibit or prevent angiogenesis. Therefore the sole administration of such proteases to an individual may not be used for preventing or treating diseases related to neoangiogenesis.

The term "medicament" as defined herein includes not only pharmaceutical products but also dietary supplements.

As used herein, "plant proteases" and "animal proteases" are intended to be proteases naturally occurring in plants or animals (non-mammalian animals) and being extracted or obtained there from. "Plant proteases" and "animal proteases" are also recombinant proteases whose encoding DNA (e.g. as cDNA) is derived or obtained from a plant and animal (comprising said DNA naturally in its genome), respectively, and cloned into appropriate vectors and expressed in a prokaryotic (e.g. bacterial) or a eukaryotic (e.g. insect cell, mammalian cell) cell culture.

"Microbial proteases", as used herein, are proteases naturally occurring in microorganisms, such as bacteria and fungi (e.g. yeast, moulds). Said proteases may, however, be isolated also from other cells or organisms, provided that said cells and organisms harbour the DNA of the microbial protease and are able to produce recombinant said protease.

It is especially preferred to use the medicament of the present invention to prevent and/or treat individuals suffering from diseases caused by high VEGF levels and associated to angiogenesis, whereby these diseases are not mainly or completely associated with increased proliferative activity. The at least one plant protease is preferably selected from the group consisting of bromelain, papain or ficin. The plant proteases preferably to be used according to the present invention are listed above.

These proteases may be obtained by recombinant expression in a host or by extraction from a plant naturally producing said proteases, whereby the extract itself may directly be used to manufacture the medicament according to the present invention. Extraction methods of the proteases are well known in the art.

Bromelain: Pineapples have had a long tradition as a medicinal plant among the natives of South and Central America. Bromelain was first introduced in Europe as a therapeutic supplement in 1957 and is mainly used in treatment of edema and inflammation (reviewed by Maurer. Cell Mol Life Sci 58 (9):1234-1245, 2001.

Papain: may be produced as a crude, dried material by collecting the latex from the fruit of the papaya tree. The latex is collected after scoring the neck of the fruit whereupon it may either dry on the fruit or drip into a container. This latex is then further dried. It is now classified as a dried, crude material. A purification step is necessary to remove contaminating substances. This purification consists of the solubilization and extraction of the active papain enzyme.

Ficin: The latex of some species of *Ficus* (Moraceae) has been traditionally used as vermifuge in Central and South America. It has been accepted that anthelmintic activity is due to a Proteolytic fraction called ficin.

Plant Proteases: Bromelain, Papain, Ficin, Ananin, Balansain, Caricain, Faustusain, Hieronymain, Karatasin, Macrodontain, Pinguinain, Cucumisin, Actinidin.

Bacterial/Microbial Proteases: According to a preferred embodiment of the present invention the protease isolated from bacteria or fungi is selected from the group consisting of Brinase (from *Aspergillus oryzae*), Nattokinase (*Bacillus subtilis* Natto), Pronase (*Streptomyces griseus*), Seaprose-S (*Aspergillus melleus*), Serrapeptase (*Bacillus Serratia* E 15), Sfericase (*Bacillus sphaericus*), Subtilisin (*Bacillus subtilis*) and Mut-Mutanase (*Aspergillus* sp.).

Microbial proteases may also be obtained by recombinant techniques or may be isolated directly from microbial cultures comprising the microorganisms which produce said proteases. Nattokinase, for instance, is obtained from Natto, a traditional Japanese food product made from fermented soybeans, or by cultures comprising organisms of a specific *Bacillus subtilis* subspecies (*Bacillus subtilis* var. Natto) which are able to produce said protease.

Serrapeptase also known as Serrapeptidase or Serratiopeptidase obtained from the microorganisms *Serratia* E 15 which lives in the gut wall of the silkworm used to aid digestion and dissolve its chrysalis. This enzyme can be used as a supplement to treat pain and inflammation naturally, and is in clinical use in parts of Asia and Europe. Serrapeptase is used as an alternative to Non Steroidal Anti-Inflammatory Drugs (NSAIDS) which are commonly used to treat arthritis and inflammation.

The animal (non-mammalian) protease is preferably isolated from the antarctic krill (crustaceae) *Euphasia superba*, Krill enzyme, Batroxobin and Lumbrokinase from the earthworm, Alfimerase, Fibrolase.

Further preferred proteases are Mutanase, Alfimerase, Fibrolase, Cucumisin, Actinidin, Ananin, Balansain, Caricain, Fastusain, Hieronymain, Karatasin, Pinguinain and macrodontain.

These proteases may be produced recombinantly by methods known in the art or obtained directly from the respective animals.

Particularly preferred medicaments comprise bromelain and/or papain as plant proteases and optionally Nattokinase as microbial protease. The preferred ratios between these proteases in a medicament according to the present invention can be found in the following table:

| Bromelain | Papain | Nattokinase |
|---|---|---|
| 100.00% | 0.00% | 0.00% |
| 75.00% | 25.00% | 0.00% |
| 16.67% | 16.67% | 66.67% |
| 25.00% | 25.00% | 50.00% |
| 0.00% | 75.00% | 25.00% |
| 75.00% | 0.00% | 25.00% |
| 25.00% | 0.00% | 75.00% |
| 16.67% | 66.67% | 16.67% |
| 50.00% | 0.00% | 50.00% |
| 0.00% | 100.00% | 0.00% |
| 0.00% | 50.00% | 50.00% |
| 0.00% | 25.00% | 75.00% |
| 33.33% | 33.33% | 33.33% |
| 25.00% | 75.00% | 0.00% |
| 0.00% | 0.00% | 100.00% |
| 50.00% | 25.00% | 25.00% |
| 25.00% | 50.00% | 25.00% |
| 50.00% | 50.00% | 0.00% |

Furthermore preferred combinations of proteases to be used in the medicament according to the present invention are:

bromelain and papain (optionally with krillenzyme, brinase, ficin, lumbrokinase, nattokinase, pronase, seaprose-S, serrapeptase, sfericase, subtilisin and/or batroxobin), bromelain and ficin (optionally with krillenzyme, brinase, papain, lumbrokinase, nattokinase, pronase, seaprose-S, serrapeptase, sfericase, subtilisin and/or batroxobin), bromelain and nattokinase (optionally with krillenzyme, brinase, ficin, lumbrokinase, papain, pronase, seaprose-S, serrapeptase, sfericase, subtilisin and/or batroxobin), bromelain and brinase (optionally with krillenzyme, papain, ficin, lumbrokinase, nattokinase, pronase, seaprose-S, serrapeptase, sfericase, subtilisin and/or batroxobin), bromelain and seaprose (optionally with krillenzyme, brinase, ficin, lumbrokinase, nattokinase, pronase, papain, serrapeptase, sfericase, subtilisin and/or batroxobin), bromelain and sfericase (optionally with krillenzyme, brinase, ficin, lumbrokinase, nattokinase, pronase, seaprose-S, serrapeptase, sfericase, subtilisin and/or batroxobin), bromelain and subtilisin (optionally with krillenzyme, brinase, ficin, lumbrokinase, nattokinase, pronase, seaprose-S, serrapeptase, sfericase, papain and/or batroxobin), bromelain and krillenzyme (optionally with brinase, ficin, lumbrokinase, nattokinase, papain, pronase, seaprose-S, serrapeptase, sfericase, subtilisin and/or batroxobin), bromelain and batroxobin (optionally with krillenzyme, brinase, ficin, lumbrokinase, nattokinase, pronase, seaprose-S, serrapeptase, sfericase, subtilisin and/or papain), bromelain and lumbrokinase (optionally with krillenzyme, brinase, ficin, papain, nattokinase, pronase, seaprose-S, serrapeptase, sfericase, subtilisin and/or batroxobin);

papain and ficin (optionally with krillenzyme, brinase, bromelain, lumbrokinase, nattokinase, pronase, seaprose-S, serrapeptase, sfericase, subtilisin and/or batroxobin), papain and nattokinase (optionally with krillenzyme, brinase, bromelain, lumbrokinase, ficin, pronase, seaprose-S, serrapeptase, sfericase, subtilisin and/or batroxobin), papain and brinase (optionally with krillenzyme, ficin, bromelain, lumbrokinase, nattokinase, pronase, seaprose-S, serrapeptase, sfericase, subtilisin and/or batroxobin), papain and seaprose (optionally with krillenzyme, brinase, bromelain, lumbrokinase, nattokinase, pronase, ficin, serrapeptase, sfericase, subtilisin and/or batroxobin), papain and sfericase (optionally with krillenzyme, brinase, bromelain, lumbrokinase, nattokinase, pronase, seaprose-S, serrapeptase, ficin, subtilisin and/or batroxobin), papain and subtilisin (optionally with krillenzyme, brinase, bromelain, lumbrokinase, nattokinase, pronase, seaprose-S, serrapeptase, sfericase, ficin and/or batroxobin), papain and krillenzyme (optionally with krillenzyme, brinase, bromelain, lumbrokinase, nattokinase, ficin, pronase, seaprose-S, serrapeptase, sfericase, subtilisin and/or batroxobin), papain and batroxobin (optionally with krillenzyme, brinase, bromelain, lumbrokinase, nattokinase, pronase, seaprose-S, serrapeptase, sfericase, subtilisin and/or ficin), papain and lumbrokinase (optionally with krillenzyme, brinase, bromelain, ficin, nattokinase, pronase, seaprose-S, serrapeptase, sfericase, subtilisin and/or batroxobin);

ficin and nattokinase (optionally with krillenzyme, brinase, bromelain, papain, lumbrokinase, pronase, seaprose-S, serrapeptase, sfericase, subtilisin and/or batroxobin), ficin and brinase (optionally with krillenzyme, nattokinase, bromelain, papain, lumbrokinase, pronase, seaprose-S, serrapeptase, sfericase, subtilisin and/or batroxobin), ficin and seaprose (optionally with krillenzyme, brinase, bromelain, papain, lumbrokinase, pronase, nattokinase, serrapeptase, sfericase, subtilisin and/or batroxobin), ficin and sfericase (optionally with krillenzyme, brinase, bromelain, papain, lumbrokinase, pronase, seaprose-S, serrapeptase, nattokinase, subtilisin and/or batroxobin), ficin and subtilisin (optionally with krillenzyme, brinase, bromelain, papain, lumbrokinase, pronase, seaprose-S, serrapeptase, sfericase, nattokinase and/or batroxobin), ficin and krillenzyme (optionally with natookinase, brinase, bromelain, papain, lumbrokinase, pronase, seaprose-S, serrapeptase, sfericase, subtilisin and/or batroxobin), ficin and batroxobin (optionally with krillenzyme, brinase, bromelain, papain, lumbrokinase, pronase, seaprose-S, serrapeptase, sfericase, subtilisin and/or nattokinase), ficin and lumbrokinase (optionally with krillenzyme, brinase, bromelain, papain, nattokinase, pronase, seaprose-S, serrapeptase, sfericase, subtilisin and/or batroxobin);

nattokinase and brinase (optionally with krillenzyme, lumbrokinase, bromelain, papain, ficin, pronase, seaprose-S, serrapeptase, sfericase, subtilisin and/or batroxobin), nattokinase and seaprose (optionally with krillenzyme, lumbrokinase, bromelain, papain, ficin, brinase, serrapeptase, sfericase, subtilisin and/or batroxobin), nattokinase and sfericase (optionally with krillenzyme, lumbrokinase, bromelain, papain, ficin, pronase, seaprose-S, serrapeptase, brinase, subtilisin and/or batroxobin), nattokinase and subtilisin (optionally with krillenzyme, lumbrokinase, bromelain, papain, ficin, pronase, seaprose-S, serrapeptase, sfericase, brinase and/or batroxobin), nattokinase and krillenzyme (optionally with brinase, lumbrokinase, bromelain, papain, ficin, pronase, seaprose-S, serrapeptase, sfericase, subtilisin and/or batroxobin), nattokinase and batroxobin (optionally with krillenzyme, lumbrokinase, bromelain, papain, ficin, pronase, seaprose-S, serrapeptase, sfericase, subtilisin and/or brinase), nattokinase and lumbrokinase (optionally with krillenzyme, brinase, bromelain, papain, ficin, pronase, seaprose-S, serrapeptase, sfericase, subtilisin and/or batroxobin), brinase and seaprose (optionally with krillenzyme, nattokinase, bromelain, papain, ficin, pronase, lumbrokinase, serrapeptase, sfericase, subtilisin and/or batroxobin), brinase and sfericase (optionally with krillenzyme, nattokinase, bromelain, papain, ficin, pronase, lumbrokinase, serrapeptase, seaprose, subtilisin and/or batroxobin), brinase and subtilisin (optionally with krillenzyme, nattokinase, bromelain, papain, ficin, pronase, lumbrokinase, serrapeptase, sfericase, seaprose and/or batroxobin), brinase and krillenzyme (optionally with seaprose, nattokinase, bromelain, papain, ficin, pronase, lumbrokinase, serrapeptase, sfericase, subtilisin and/or batroxobin), brinase and batroxobin (optionally with krillenzyme, nattokinase, bromelain, papain, ficin, pronase, lumbrokinase, serrapeptase, sfericase, subtilisin and/or seaprose), brinase and lumbrokinase (optionally with krillenzyme, nattokinase, bromelain, papain, ficin, pronase, seaprose, serrapeptase, sfericase, subtilisin and/or batroxobin);

seaprose and sfericase (optionally with krillenzyme, nattokinase, bromelain, papain, ficin, pronase, brinase, serrapeptase, lumbrokinase, subtilisin and/or batroxobin), seaprose and subtilisin (optionally with krillenzyme, nattokinase, bromelain, papain, ficin, pronase, brinase, serrapeptase, lumbrokinase, sfericase and/or batroxobin), seaprose and krillenzyme (optionally with sfericase, nattokinase, bromelain, papain, ficin, pronase, brinase, serrapeptase, lumbrokinase, subtilisin and/or batroxobin), seaprose and batroxobin (optionally with krillenzyme, nattokinase, bromelain, papain, ficin, pronase, brinase, serrapeptase, lumbrokinase, subtilisin and/or sfericase), seaprose and lumbrokinase (optionally with krillenzyme, nattokinase, bromelain, papain, ficin, pronase, brinase, serrapeptase, sfericase, subtilisin and/or batroxobin);

sfericase and subtilisin (optionally with krillenzyme, nattokinase, bromelain, papain, ficin, pronase, brinase, serrapeptase, seaprose, lumbrokinase and/or batroxobin), sfericase and krillenzyme (optionally with subtilisin, nattokinase, bromelain, papain, ficin, pronase, brinase, serrapeptase, sfericase, seaprose, lumbrokinase and/or batroxobin), sfericase and batroxobin (optionally with krillenzyme, nattokinase, bromelain, papain, ficin, pronase, brinase, serrapeptase, sfericase, subtilisin, lumbrokinase and/or seaprose), sfericase and lumbrokinase (optionally with krillenzyme, nattokinase, bromelain, papain, ficin, pronase, brinase, serrapeptase, subtilisin, seaprose and/or batroxobin);

subtilisin and krillenzyme (optionally with lumbrokinase, nattokinase, bromelain, papain, ficin, pronase, brinase, serrapeptase, sfericase, seaprose and/or batroxobin), subtilisin and batroxobin (optionally with lumbrokinase, nattokinase, bromelain, papain, ficin, pronase, brinase, serrapeptase, sfericase, seaprose and/or krillenzyme), subtilisin and lumbrokinase (optionally with krillenzyme, nattokinase, bromelain, papain, ficin, pronase, brinase, serrapeptase, sfericase, seaprose and/or batroxobin);

krillenzyme and batroxobin (optionally with substilin, nattokinase, bromelain, papain, ficin, pronase, brinase, serrapeptase, sfericase, seaprose and/or lumbrokinase), krillenzyme and lumbrokinase (optionally with krillenzyme, nattokinase, bromelain, papain, ficin, pronase, brinase, serrapeptase, sfericase, seaprose and/or batroxobin), batroxobin and lumbrokinase (optionally with krillenzyme, nattokinase, bromelain, papain, ficin, pronase, brinase, serrapeptase, sfericase, seaprose and/or krillenzyme).

These combinations of proteases may be further combined with at least one protease selected from the group consisting of mutanase, alfimerase, fibrolase, cucumisin, actinidin, ananin, balansain, caricain, fastusain, hieronymain, karatasin, pinguinain and macrodontain.

Particularly preferred medicaments of the present invention comprise bromelain in combination with papain, ficin, nattokinase, brinase, seaprose, sfericase, subtilisin, krillenzyme, batroxobin, lumbrokinase.

In the medicament of the present invention each of the at least two proteases is present in a relative amount of at least 10%, preferably at least 15%, in relation to the total amount of proteases present in said medicament.

According to another preferred embodiment of the present invention the at least two proteases are comprised in the medicament in an amount from 5 to 10, preferably from 10 to 90% w/w, preferably from 20 to 80% w/w, more preferably from 30 to 70% w/w.

The at least one protease is preferably administered to an individual in an amount of 2 to 50 mg/kg, preferably 5 to 20 mg/kg body weight. As mentioned above the amount of proteases administered ranges from 3 to 300 U/kg body weight, preferably 6 to 150 U/kg body weight, more preferably 15 to 60 U/kg body weight. Furthermore the proteases may be administered in a amount of 3 to 150 U/kg body weight or 3 to 60 U/kg body weight. The medicament may preferably further comprise at least one pharmaceutical acceptable carrier, diluents and/or excipients, preferably a binder, filler, a disintegrant, a lubricant, a preservative and/or a coating.

Depending on the pharmaceutical formulation of the medicament according to the present invention various other substances like excipients, coatings etc. may be used.

The medicament of the present invention is preferably adapted for oral administration.

According to a preferred embodiment of the present invention the medicament is provided in a pharmaceutical form selected from the group consisting of drops, spray, tablets, preferably soluble tablets, effervescent tablets, gastro-resistant tablets and sublingual tablets, capsules, preferably gastro-resistant capsules, powders, granules, oral liquids, oral drops and suppositories.

The medicament is adapted for oral administration. This mode of administration is non-invasive and therefore allows a repeated administration (without harming the patient) of the medicament as proven for about 50 years (Ransberger. Erfahrungsheilkunde 1:14-17, 1971).

The medicament of the present invention may be specially formulated for administration in solid or liquid form, including those adapted for oral administration, for example, drenches (aqueous or non-aqueous solutions or suspensions), tablets, boluses, powders, granules, pastes for application to the tongue.

The medicament of the present invention may also be provided for other routes of administration:
(1) Parenteral administration, for example, by subcutaneous, intramuscular or intravenous injection as, for example, a sterile solution or suspension;
(2) Topical application, for example, as a cream, ointment or spray applied to the skin; or
(3) Intrarectally, for example, as a pessary, cream or foam.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

Examples of materials which can serve as pharmaceutically acceptable carriers include:
(1) Sugars, such as lactose, glucose and sucrose;
(2) Starches, such as corn starch and potato starch;
(3) Cellulose, and its derivatives, such as sodium carboxymethyl cellulose, ethyl cellulose and cellulose acetate;
(4) powdered tragacanth;
(5) malt;
(6) gelatine;
(7) talc;
(8) excipients, such as cocoa butter and suppository waxes;
(9) oils, such as peanut oil, cottonseed oil, safflower oil, sesame oil, olive oil, corn oil and soybean oil;
(10) glycols, such as propylene glycol;
(11) polyols, such as glycerine, sorbitol, mannitol and polyethylene glycol;
(12) esters, such as ethyl oleate and ethyl laurate;
(13) agar;
(14) buffering agents, such as magnesium hydroxide and aluminium hydroxide;
(15) alginic acid;
(16) pyrogen-free water;
(17) isotonic saline;
(18) Ringer's solution;
(19) ethyl alcohol;
(20) phosphate buffer solutions; and
(21) other non-toxic compatible substances employed in pharmaceutical formulations.

Wetting agents, emulsifiers and lubricants, such as sodium lauryl sulfate and magnesium stearate, as well as colouring agents, release agents, coating agents, sweetening, flavouring and perfuming agents, preservatives and antioxidants can also be present in the medicament according to the present invention.

Examples of pharmaceutically-acceptable antioxidants include:
(1) water soluble antioxidants, such as ascorbic acid, cysteine hydrochloride, sodium bisulfate, sodium metabisulfite, sodium sulfite and the like;
(2) oil-soluble antioxidants, such as ascorbyl palmitate, butylated hydroxyanisole, butylated hydroxytoluene, lecithin, propyl gallate, alpha-tocopherol, and the like; and
(3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration.

The amount of active ingredient which can be combined with a carrier material to produce a single dosage form will generally be that amount of the compound which produces a therapeutic effect.

Methods of preparing the medicaments and formulations according to the present invention include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product. Formulations of the invention suitable for oral administration may be in the form of capsules, cachets, pills, tablets, lozenges (using a flavoured basis, usually sucrose and acacia or tragacanth), powders, granules, or as a solution or a suspension in an aqueous or non-aqueous liquid, or as an oil-in-water or water-in-oil liquid emulsion, or as a syrup, or as pastilles (using an inert base, such as gelatine and glycerine, or sucrose and acacia), each containing a predetermined amount of a protease combination of the present invention as active ingredients.

The proteases of the present invention may also be administered as a bolus, electuary or paste. In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following:

(1) fillers or extenders, such as starches, lactose, sucrose, glucose, mannitol, and/or silicic acid;
(2) Binders, such as, for example, carboxymethylcellulose, alginates, gelatine, polyvinyl pyrrolidone, sucrose and/or acacia;
(3) Humectants, such as glycerol;
(4) Disintegrating agents, such as agaragar, calcium carbonate, potato or tapioca starch, alginic acid, certain silicates, and sodium carbonate;
(5) Solution retarding agents, such as paraffin;
(6) Absorption accelerators, such as quaternary ammonium compounds;
(7) wetting agents, such as, for example, cetyl alcohol and glycerol monostearate;
(8) Absorbents, such as kaolin and bentonite clay;
(9) Lubricants, such a talc, calcium stearate, magnesium stearate, solid polyethylene glycols, sodium lauryl sulfate, and mixtures thereof;
and
(10) Colouring agents.

In the case of capsules, tablets and pills, the pharmaceutical compositions may also comprise buffering agents. Solid compositions of a similar type may also be employed as fillers in soft and hard-filled gelatine capsules using such excipients as lactose or milk sugars, as well as high molecular weight polyethylene glycols and the like.

A tablet may be made by compression or moulding, optionally with one or more accessory ingredients. Compressed tablets may be prepared using binder (for example, gelatine or hydroxypropylmethyl cellulose), lubricant, inert diluents, preservative, disintegrate (for example, sodium starch glycolate or cross-linked sodium carboxymethyl cellulose), surface-active or dispersing agent. Moulded tablets may be made by moulding in a suitable machine a mixture of the powdered compound moistened with inert liquid diluents. The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract or, optionally, in a delayed manner.

Examples of embedding compositions which can be used include polymeric substances and waxes. The proteases can also be in micro-encapsulated form, if appropriate, with one or more of the above-described excipients. Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, polyethylene glycols and fatty acid esters of sorbitan, and mixtures thereof. Besides inert diluents, the oral compositions can also include adjuvant such as wetting agents, emulsifying and suspending agents, sweetening, flavouring, colouring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agaragar and tragacanth, and mixtures thereof.

Formulations of the pharmaceutical compositions of the invention for rectal administration may be presented as a suppository, which may be prepared by mixing the proteases of the invention with one or more suitable non-irritating excipients or carriers comprising, for example, cocoa butter, polyethylene glycol, a suppository wax or a salicylate, and which is solid at room temperature, but liquid at body temperature and, therefore, will melt in the rectum cavity and release the active compound. Formulations of the present invention which are suitable for rectal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The proteases may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffin, starch, tragacanth, cellulose derivatives, polyethylene glycols, silicones, bentonites, silicic acid, talc and zinc oxide, or mixtures thereof.

Powders and sprays can contain, in addition to the proteases of this invention, excipients such as lactose, talc, silica acid, aluminium hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the proteases of the present invention to the body. Such dosage forms can be made by dissolving or dispersing the proteases in the proper medium.

Absorption enhancers can also be used to increase the flux of the proteases across the skin. The rate of such flux can be controlled by either providing a rate controlling membrane or dispersing the compound in a polymer matrix or gel.

Pharmaceutical compositions of this invention suitable for parenteral administration comprise the proteases of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvant such as preservatives, wetting agents, emulsifying agents and dispersing agents. Prevention of the action of microorganisms upon the subject compositions may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminium monostearate and gelatine. In some cases, in order to prolong the effect of a drug, it is desirable to slow the absorption of the drug from subcutaneous or intramuscular injection.

This may be accomplished by the use of a liquid suspension of crystalline or amorphous material having poor water solubility. Alternatively, delayed absorption of a parenterally-administered drug form is accomplished by dissolving or suspending the drug in an oil vehicle. Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides).

Depot injectable formulations are also prepared by entrapping the drug in liposomes or micro-emulsions which are compatible with body tissue. When the proteases of the present invention are administered as pharmaceuticals, to humans and animals, they can be given per se or as a pharmaceutical composition containing, for example, 0.1 to 99.5% (more preferably, 0.5 to 90%) of the proteases in combination with a pharmaceutically acceptable carrier. The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by, suppositories. Oral and topical administrations are preferred. The phrases "parenteral administration" and "administered parenterally" as used herein mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The medicament of the present invention may be administered to humans and other animals for therapy by any suitable route of administration, including orally, nasally, as by, for example, a spray, rectally, parenterally, intracisternally and topically, as by powders, ointments or drops, including buccally and sublingually.

Regardless of the route of administration selected, the proteases of the present invention, which may be used in a suitable hydrated form, and/or the pharmaceutical compositions of the present invention, are formulated into pharmaceutically-acceptable dosage forms by conventional methods known to those of skilled in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular protease of the present invention employed, the route of administration, the time of administration, the rate of excretion of the particular compound being employed, the duration of the treatment, other drugs, compounds and/or materials used in combination with the proteases employed, the age, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the proteases of the invention employed in the pharmaceutical composition at levels lower than that required in order to achieve the desired therapeutic effect and gradually increase the dosage until the desired effect is achieved.

While it is possible for the proteases of the present invention to be administered alone, it is preferable to administer the proteases as a pharmaceutical formulation (composition).

According to another preferred embodiment of the present invention the medicament further comprises at least one further active ingredient.

Said active ingredient may be any one which may support the prevention and the treatment of angiogenic diseases with the proteases according to the present invention. However, it is of course also possible to add active ingredients exhibiting other effects than said proteases.

According to another preferred embodiment of the present invention the medicament comprises at least one preferably at least two (three or even four) proteases selected from the group consisting of:

Plant proteases: bromelain, papain, ficin, Ananin, Balansain, Caricain, Faustusain, Hieronymain, Karatasin, Macrodontain, Pinguinain, Cucumisin, Actinidin Proteases from bacteria: Nattokinase, Pronase, Serrapeptase, Sfericase, and Subtilisin Proteases from fungi: Brinase; Seaprose-S, Mutanase Proteases from Crustaceae: Krillenzym Proteases from earth worm: lumbrokinase Proteases from snakes: alfimerase, fibrolase The present invention is further illustrated by the following figures and examples.

FIG. 7 (right) shows the inhibition of VEGF induced tube formation in HUVEC. Bromelain, ficin, nattokinase, papain and serrapeptase, but not chymotrypsin or trypsin inhibited formation of tubes almost to the same extend as in untreated HUVEC.

EXAMPLES

BPH
Materials:

Bromelain from Pineapple stem with an activity of 3.51 U/mg was obtained from Sigma Aldrich, Austria. Nattokinase with an activity of 10.000U/ml was purchased from Japan Bio Science Laboratory Co, Ltd. Papain from Carica Papaya with an activity of >3U/mg was obtained from Sigma Aldrich, Austria Methods:
Toxicity-Test The antiproliferative activity of Bromelain, Nattokinase and Papain was assessed using a Lactate Dehydrogenase (LDH) Assay. Human Umbilical Vein Endothelial Cells (HUVEC) from semi-confluent cultures were harvested by treatment with trypsin, seeded at a density of 2500 cells/well into 96-well microplates, previously coated with human fibronectin. In order to allow proper attachment, cells were incubated for 24 hours in Endothelial Basal medium 2MV (Cambrex Biochemicals) containing 10% Fetal Calf Serum, 60 µg/ml Endothelial cell Growth Supplement, hrEGF, hrFGF2, hrIGF, hrVEGF, Ascorbic Acid and Heparin. After attachment, cells were starved by incubation at 37° C./95% humidity in Medium 199+10% Fetal Calf Serum (FCS) without growth factors. After 24 hours, the supernatant was replaced by Medium 199 containing 10% FCS, VEGF and varying concentrations of the enzymes. After an incubation period of 48 hours, supernatant was harvested and an LDH assay was performed according to the instructions of the manufacturer (Promega, Germany): 50 µl aliquots from all wells were transferred to a fresh 96-well flat-bottom (enzymatic assay) plate. The Assay Buffer was added to the Substrate Mix and mixed gently. 50 µl of reconstituted Substrate Mix was added to each well. The plate was incubated for 30 minutes at room temperature. 50 µl of Stop Solution was added to each well. Within one hour, optical density was measured at 490 nm with a reference wavelength of 620 nm. Results are expressed as % untreated control.

Figure 1:
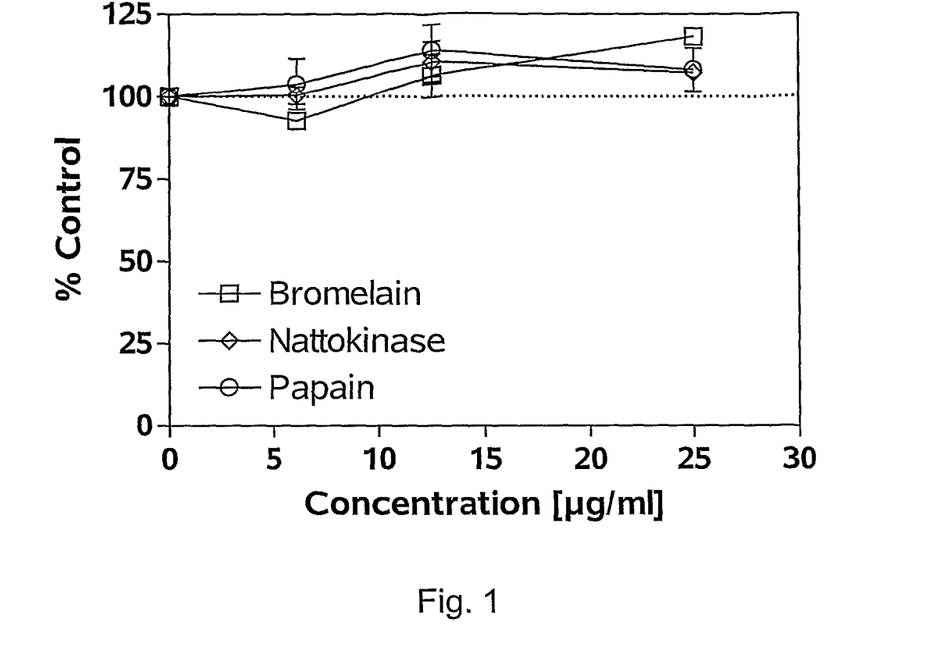
FIG. 1 shows the LDH release into the supernatant of enzyme treated HUVEC.

The results are shown in FIG. 1. They clearly demonstrate that Bromelain, Nattokinase and Papain up to a level of including 25 µg/ml did not show toxic effects on HUVEC after 2 days of incubation.

Antiproliferative Activity

The antiproliferative activity of Bromelain, Nattokinase and Papain and their mixtures was assessed using an 3-(4,5-dimethylthiazol-2-yl)-2,5-diphenyltetrazoliumbromide (MTT) assay. Human Umbilical Vein Endothelial Cells (HUVEC) from semiconfluent cultures were harvested by treatment with trypsin seeded at a density of 1000 cells/well into 96-well microplates, previously coated with human fibronectin. In order to allow proper attachment, cells where incubated for 24 hours in Endothelial Basal medium 2MV (Cambrex Biochemicals) containing 10% Fetal Calf Serum, 60 µg/ml Endothelial cell Growth Supplement, hrEGF, hrFGF2, hrIGF, hrVEGF, Ascorbic Acid and Heparin. After attachment, cells were starved by incubation at 37° C./95% humidity in Medium 199+10% Fetal Calf Serum (FCS) without growth factors. After 24 hours, the supernatant was replaced by Medium 199 containing 10% FCS and varying concentrations of Bromelain, Nattokinase or Papain. Cells were incubated further 48 hours at 37° C./95% humidity. The MTT Assay was carried out using an EZ4U MTT Kit (Biomedica, Austria; according to the instructions of the manufacturer). Optical density was measured at 450 nm with a reference wavelength of 620 nm. Results are expressed as % untreated control or % proliferation with 100% being the proliferation of the VEGF treated control.

Figure 2:
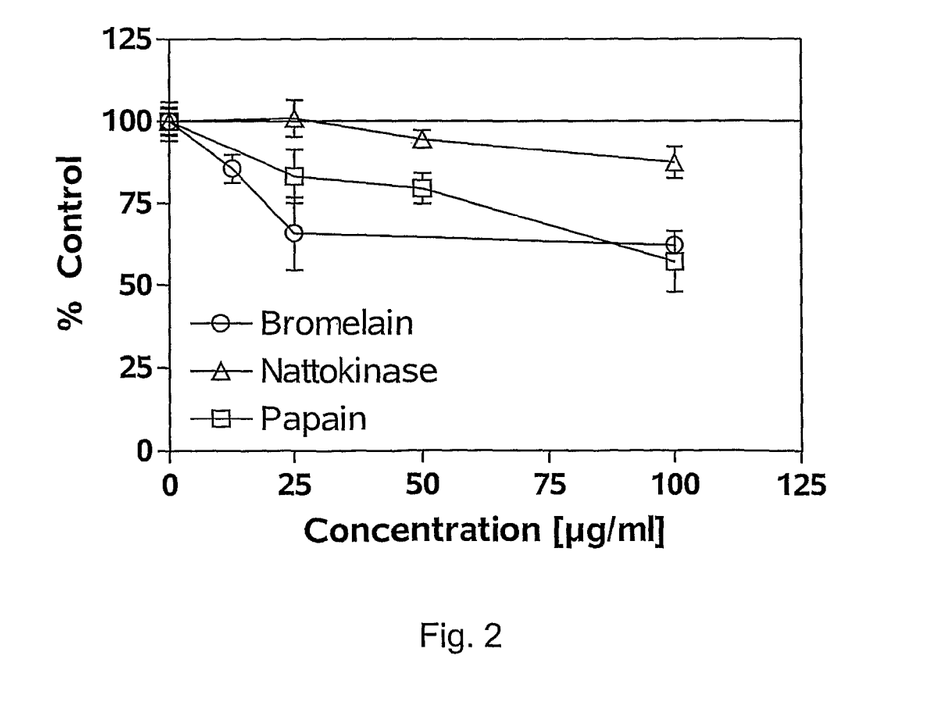
FIG. 2 shows a MTT assay with enzyme treated HUVEC.

The results of the concentration-response experiments are shown in FIG. 2. They demonstrate a clear antiproliferative effect of Bromelain, Nattokinase and Papain with Bromelain and Papain reaching 75% growth at concentrations as low as 25 µg/ml. Taken together with the results from the LDH release test, these data point towards a clear antiproliferative effect, but not cytotoxic activity of Bromelain, Nattokinase or Papain on HUVEC.

Antiangiogenic Activity

Antiangiogenic activity on HUVEC was assessed using a tube formation assay. Growth factor reduced Matrigel (Becton Dickinson, Vienna) was thawed at a temperature of 4° C. 50 µl per well were pipetted into the wells of a 96-well microplate. The plate was left at 4° C. for 24 hours. Prior to the experiment, the plate was incubated for 30-60 minutes at 37° C. to solidify the gel. HUVEC where incubated for 24 hours with Medium 199 containing 2% FCS. Cells were harvested by treatment with trypsin and seeded into Matrigel coated 96 well microplates at a density of 10.000 cells per well. Drugs were added to the desired concentrations and cells where incubated in absence or presence of 5 ng VEGF/ml. After further 6 hrs, wells were photographed. The total length of tubes was determined using the ImageJ Software (National Institute of Health, Bethesda, USA).

Results:
Results:

Example 1

Growth Inhibition of HUVEC by Enzymes

The results of the mixtures are shown in table 1. A clear anti-proliferative effect can be seen.

TABLE 1

Growth inhibition of HUVEC of combinations of Bromelain, Nattokinase and Papain in presence of VEGF.

| Bromelain | Nattokinase | Papain | % Proliferation |
|---|---|---|---|
| 0.00% | 0.00% | 100.00% | 75.45% |
| 75.00% | 0.00% | 25.00% | 89.09% |
| 16.67% | 16.67% | 66.67% | 91.82% |
| 25.00% | 75.00% | 0.00% | 94.55% |
| 66.67% | 16.67% | 16.67% | 96.82% |

Example 2

Figure 3:
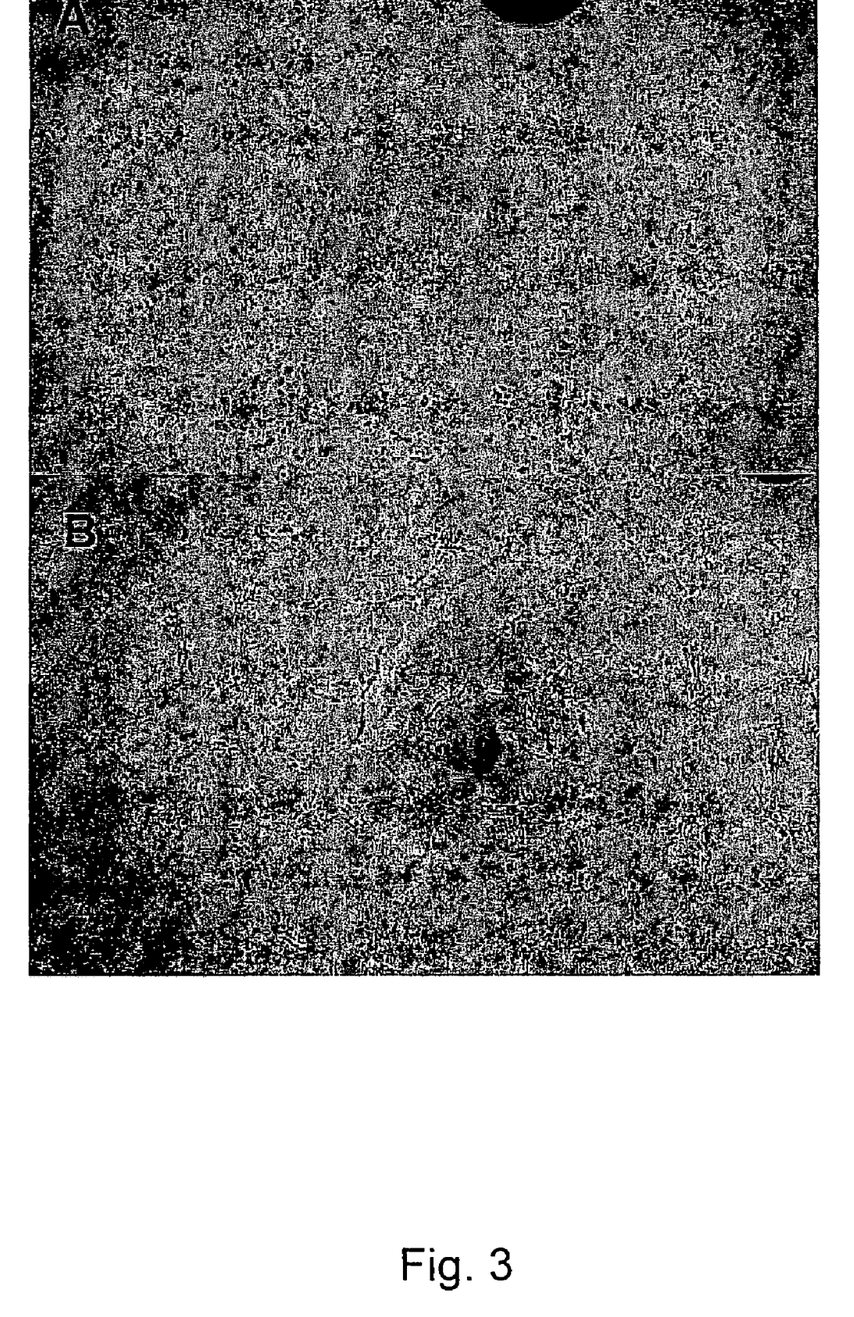
FIG. 3(A) shows the inhibiton of VEGF induced tube formation by combination of 25% Bromelain, 50% nattokinase and 25% papain.
FIG. 3(B) shows the control treated with VEGF only. Whereas in the VEGF control a narrow pattern of formed tubes is visible, the enzyme treated sample shows wide areas of non-tube formation indicating antiangiogenic activity of the enzyme cocktail.

Tube Formation of HUVEC Incubated with enzymes Bromelain, Nattokinase and Papain The results of the tube formation assays of mixtures are shown in FIG. 3 as well as table 2.

TABLE 2

Inhibition of tube formation in % in HUVECs in presence of VEGF.

| Bromelain | Nattokinase | Papain | % inhibition of tube formation |
|---|---|---|---|
| 75.00% | 25.00% | 0.00% | 98.11% |
| 16.67% | 16.67% | 66.67% | 93.52% |
| 25.00% | 25.00% | 50.00% | 87.75% |
| 0.00% | 75.00% | 25.00% | 87.42% |
| 75.00% | 0.00% | 25.00% | 86.34% |
| 25.00% | 0.00% | 75.00% | 83.77% |
| 16.67% | 66.67% | 16.67% | 83.65% |
| 50.00% | 0.00% | 50.00% | 82.73% |
| 0.00% | 50.00% | 50.00% | 80.01% |
| 0.00% | 25.00% | 75.00% | 78.26% |
| 33.33% | 33.33% | 33.33% | 74.14% |
| 25.00% | 75.00% | 0.00% | 61.57% |
| 50.00% | 25.00% | 25.00% | 47.78% |
| 0.00% | 0.00% | 100.00% | 39.86% |

Results are shown as % inhibition of tube formation with 0% equating tube formation in samples treated with only VEGF.

Table 2 shows the tube lengths expressed as % inhibition of tube formation
Results clearly indicate:
1. Tube formation is inhibited by mixtures of Bromelain, Nattokinase and Papain;
2. The combination of Bromelain, Nattokinase and Papain has a greater effect than the drugs alone.

FIG. 3 (A) shows the combination 25% Bromelain, 50% Nattokinase and 25% Papain. (B) shows the control treated with VEGF. Whereas in the VEGF control a narrow pattern of formed tubes is visible (arrows), the enzyme treated sample shows wide areas of non-tube formation indicating antiangiogenic activity of the enzyme cocktail.

Example 3

The influence of preparations comprising bromelain in combination with other enzymes on Human Prostate Endothelial Cells (HProsEC) has been analyzed analogous to example 2 with minor modifications. Briefly cells where starved for 24 hrs in Endothelial Basal Medium-2 (MV) (Lonza, Verviers) supplemented with ascorbic acid and hydrocortisone. Cells where seeded at a density of 10.000 per well into a matrigel coated 96-well microtiter plates and incubated in absence or presence of 5 ng VEGF/ml with combinations of enzymes (either 100% bromelain or 50% enzyme and 50% bromelain at 12.5 µg/ml total). After 6 hrs, tubes where photographed and measured using ImageJ Software (National Institute of Health, Bethesda, USA). The following results have been obtained:

TABLE 4

These results clearly show that a protease combination comprising bromelain and a further protease leads to an increased inhibition of tube formation.

| enzyme | % Inhibition Tube Formation gene enzyme | % Inhibition Tube Formation enzyme + Bromelain |
|---|---|---|
| Brinase | 21.00% | 81.00% |
| Pronase | 94.25% | 99.00% |
| Subtilisin | 27.00% | 100.00% |
| Streptokinase | 29.00% | 80.00% |
| Protease Typ X | 96.70% | 100.00% |
| Protease Typ XIII | 60.60% | 98.00% |
| Bromelain | 68.00% | — |

Example 4

Tube Formation of HUVEC in Presence of Proteases from Animals

Proteases from Animals

To test whether tube formation is inhibited because of cell detachment, HUVEC were treated with chymotrypsin and trypsin, two proteolytic enzymes widely used in cell detachment. Results are shown in table 3. Neither chymotrypsin nor trypsin showed a significant effect.

TABLE 3

% tube formation in HUVEC after treatment with VEGF and trypsin or chymotrypsin

| Concentration [ug/ml] | Chymotrypsin | Trypsin |
|---|---|---|
| 0 | 100.00% | 100.00% |
| 2.5 | 112.40% | 112.82% |
| 5 | 95.94% | 112.23% |
| 10 | 81.16% | 95.22% |
| 20 | 131.18% | 127.87% |

A significant decrease in proliferation was detected in human umbilical endothelial cells after treatment with Bromelain, Nattokinase and Papain alone or in combination with concentration ranges between 25 and 100 µg/ml.

A relatively low toxicity of Bromelain, Nattokinase and Papain has been demonstrated, particularly at the levels shown to exhibit an antiproliferative effect. Concentrations of up to 50 µg/ml exhibited no toxic effect HUVEC after 2 days incubation at 37° C.

Example 5

Influence of Enzyme Mixture on VEGF Concentration in Human Blood

In this example the effect of an enzyme therapy (Mixture of Nattokinase, Bromelain, Papain) on the amount of VEGF concentration in blood was studied. It could be shown (see results below) that the enzyme therapy significantly reduces elevated VEGF concentration in human blood.

Trial was performed as randomized, open label, multicentre pilot study on 111 diabetic type 2 patients of both genders in two parallel, comparable groups. 54 patients got Rutozym™ (Nattokinase (20 000 FU/gm) 25 mg Bromelain (2450 GDU/gm) 90 mg Papain N.F. (2.400 USP Units/mg). 100 mg, Marlyn Nutraceuticals, USA) for 4 weeks. VEGF concentrations in patients' plasma were tested before supplementation and right after 4 weeks of supplementation.

Patients served themselves as self-control with their initial values.

Figure 4:
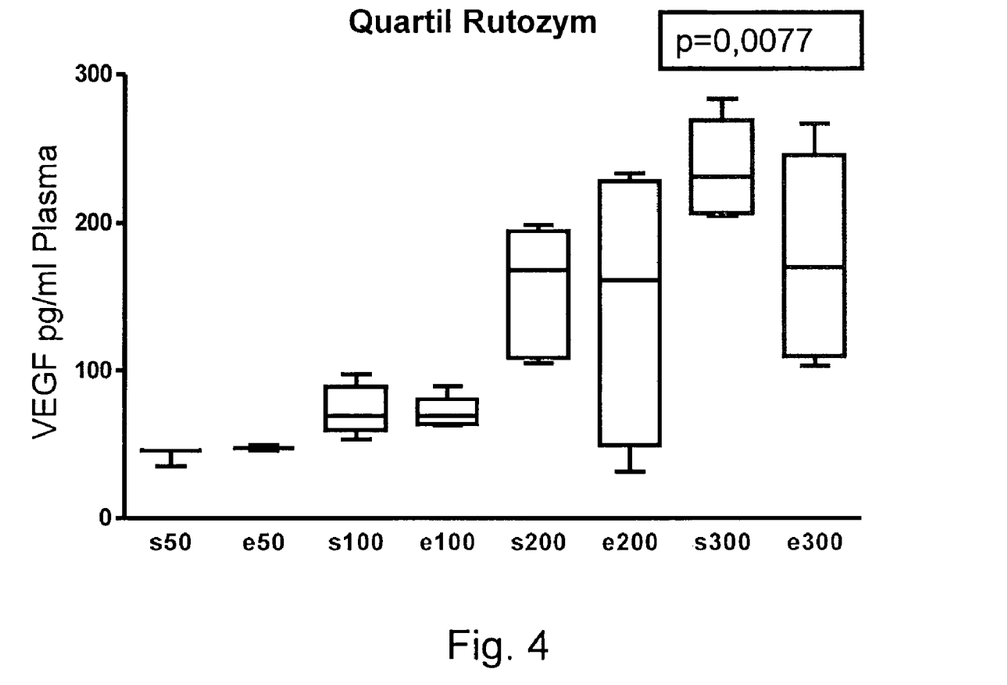
FIG. 4 shows the VEGF concentrations in blood of patients treated with Rutozym.
Figure 5:
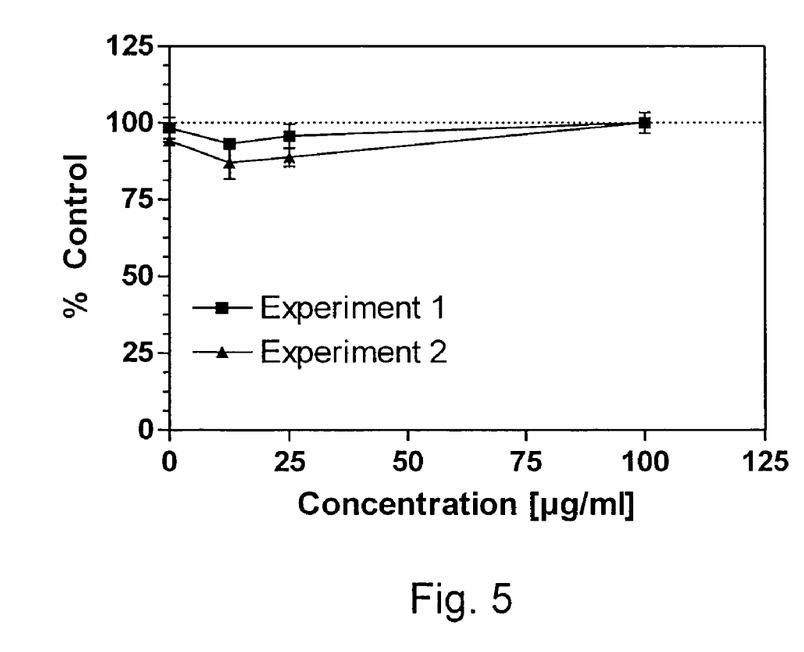
FIG. 5 shows an MTT-Assay with VEGF stimulated HUVEC and Rutosid. No inhibition of proliferation can be seen.
Figure 6:
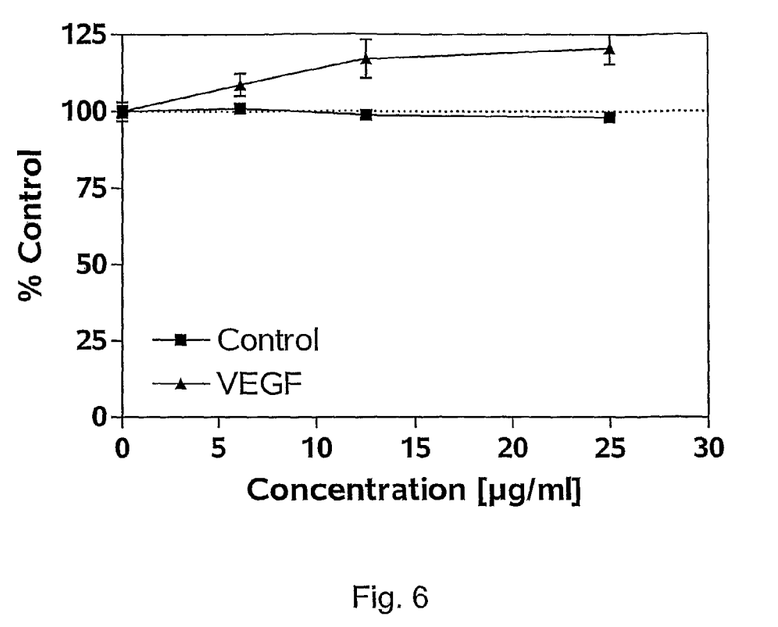
FIG. 6 shows the toxic effects of Rutosid on HUVEC. No toxic effects could be seen in quiescent HUVEC, whereas VEGF activated HUVEC show a slight effect.
Figure 7:
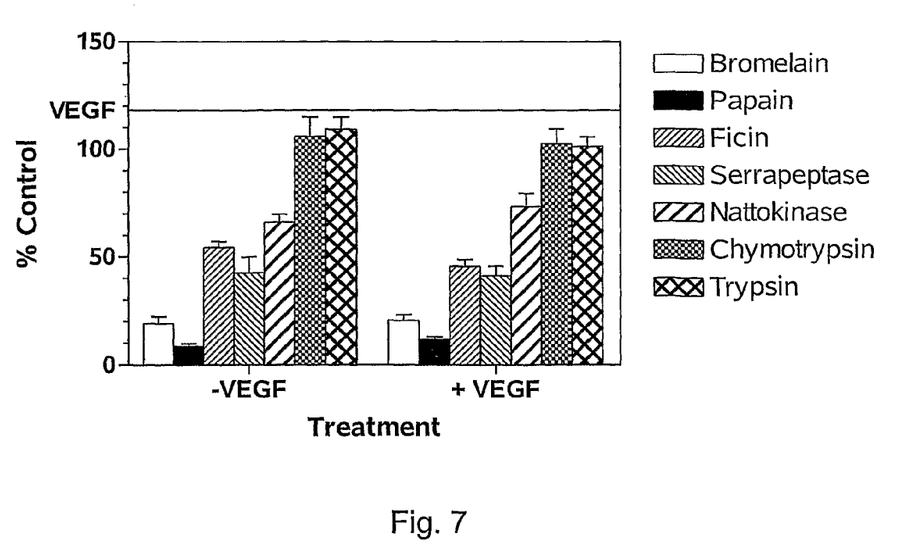
FIG. 7 (left) shows the inhibition of spontaneous tube formation in HUVEC. Bromelain, ficin, nattokinase, papain and serrapeptase, but not chymotrypsin or trypsin inhibited formation of tubes.

VEGF concentrations in blood were separated in 4 different groups (quartiles; see FIG. 4): VEGF concentration in patients blood before therapy <50 ng/ml; (s50=start <50 ng/ml; e50=end) s100: VEGF concentration <100 ng/ml before therapy; s200: <200 ng/ml before therapy and s300: >200 ng VEGF before therapy.

It could be shown that the use of a medicament according to the present invention comprising proteases of plant and/or microbial sources can be used to reduce the VEGF level in blood and, thus, be used for the treatment of diseases related to neoangiogenesis.

Conclusion

Proteolytic enzymes from plant, bacterial and fungus origin can be used to treat benign prostatic hypertrophy in mammals to reduce the progression and to cause the regression of hypertrophied prostate tissue and thereby provide remedy from obstructive symptoms associated with the disease.

Oral Enzyme therapy reduces elevated VEGF-concentration in diabetic patients but has no influence on normal VEGF-level.

Proteolytic enzymes reduce tube formation in HUVEC, induced by VEGF.

Enzyme therapy inhibits angiogenic growth factors leading to reduced vascularity, and this is the basis of its action in reducing benign prostatic hypertrophy-hyperplasia.

The invention claimed is:

1. A method for treating or preventing benign prostate hypertrophy/hyperplasia, the method comprising administering a medicament to an individual, wherein the medicament comprises at least one protease selected from the group consisting of a plant protease, a non-mammalian animal protease, and a microbial protease, and wherein the administration comprises enteric administration in an amount of 1 to 100 mg/kg body weight of the individual.

2. The method of claim 1, wherein the plant protease is selected from the group consisting of bromelain, papain, ficin, Ananin, Balansain, Caricain, Faustusain, Hieronymain, Karatasin, Macrodontain, Pinguinain, Cucumisin, Actinidin; the microbial protease is selected from the group consisting of nattokinase, brinase, seaprose, sfericase, subtilisin and mutanase; and the non-mammalian animal protease is selected from the group consisting of krillenzyme, batroxobin, lumbrokinase, alfimerase, and mutanase.

3. The method of claim 1, wherein the medicament comprises the at least one protease in an amount from 5 to 100% w/w, from 20 to 80% w/w, or from 30 to 70% w/w.

4. The method of claim 1, wherein the at least one protease is administered to the individual in an amount of 2 to 50 mg/kg, or 5 to 20 mg/kg body weight of the individual.

5. The method of claim 1, wherein the medicament further comprises at least one pharmaceutically acceptable carrier, diluent and/or excipient.

6. The method of claim 1, wherein the medicament is provided in a pharmaceutical form selected from the group consisting of drops, spray, tablets, soluble tablets, effervescent tablets, gastro-resistant tablets and sublingual tablets, capsules, gastro-resistant capsules, powders, granules, oral liquids, oral drops and suppositories.

7. The method of claim 1, wherein the medicament further comprises at least one further active ingredient.

8. The method of claim 7, wherein the at least one further active ingredient is a flavonoid and/or an antioxidant.

9. The method of claim 8, wherein the at least one further active ingredient is comprised in the medicament in an amount from 5 to 35% w/w, from 10 to 30% w/w, or from 15 to 25% w/w.

10. The method of claim 1, wherein the medicament comprises at least one protease selected from the group consisting of brinase, bromelain, ficin, lumbrokinase, nattokinase, papain, pronase, seaprose-S, serrapeptase, sfericase, subtilisin, krillenzyme and batroxobin, Mutanase, Alfimerase, Fibrolase, Cucumisin, Actinidin, Ananin, Balansain, Caricain, Fastusain, Hieronymain, Karatasin, Pinguinain and macrodontain.

11. The method of claim 5, wherein the pharmaceutically acceptable carrier, diluent and/or excipient comprises a binder, a filler, a disintegrant, a lubricant, a preservative or a coating.

* * * * *